(12) United States Patent
Dilk et al.

(10) Patent No.: US 7,494,967 B2
(45) Date of Patent: Feb. 24, 2009

(54) 3-METHYLBENZYL-ISOBUTYRATE

(75) Inventors: Erich Dilk, Holzminden (DE); Horst Surburg, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 286 days.

(21) Appl. No.: 11/568,890

(22) PCT Filed: Apr. 29, 2005

(86) PCT No.: PCT/EP2005/051967
§ 371 (c)(1), (2), (4) Date: Nov. 9, 2006

(87) PCT Pub. No.: WO2005/110967
PCT Pub. Date: Nov. 24, 2005

(65) Prior Publication Data
US 2007/0191258 A1 Aug. 16, 2007

(30) Foreign Application Priority Data
May 12, 2004 (DE) .................. 10 2004 023 346

(51) Int. Cl.
*A61K 8/37* (2006.01)
*A61K 8/34* (2006.01)

(52) U.S. Cl. .............................. 512/21; 512/20; 512/26
(58) Field of Classification Search .................. 512/1, 512/20, 21, 26
See application file for complete search history.

(56) References Cited

FOREIGN PATENT DOCUMENTS

| EP | 0056500 | 7/1982 |
|---|---|---|
| EP | 0217159 | 4/1987 |

OTHER PUBLICATIONS

Steffan Arctander, Perfume and Flavor Chemicals, 1969, Selbstverlag, Montclair, NJ, XP002336565.
Steffan Arctander, Perfume and Flavor Chemicals, 1969, Selbstverlag, Montclair, NJ, XP002336566.
Steffan Arctander, Perfume and Flavor Chemicals, 1969, Selbstverlag, Montclair, NJ, XP002336567.

*Primary Examiner*—Mark Eashoo
*Assistant Examiner*—Peter F Godenschwager
(74) *Attorney, Agent, or Firm*—Roylance, Abrams, Berdo & Goodman, L.L.P.

(57) ABSTRACT

3-Methylbenzyl isobutyrate is described, as is the use thereof as an odoriferous substance, in particular for imparting a green fruity head note to an odoriferous substance mixture.

4 Claims, No Drawings

3-METHYLBENZYL-ISOBUTYRATE

FIELD OF THE INVENTION

The present invention relates in particular to 3-methylbenzyl isobutyrate, to odoriferous substance mixtures comprising 3-methylbenzyl isobutyrate, to the use of 3-methylbenzyl isobutyrate as an odoriferous substance and to processes for producing 3-methylbenzyl isobutyrate.

Due to the generally inadequate availability of many natural odoriferous substance components, the need to adapt to changing fashions in taste and the ever increasing demand for new odoriferous substances, which, alone or in the form of compositions, constitute useful fragrances or perfumes with interesting fragrance notes, a need still remains for new compounds with useful odoriferous substance qualities. Particularly sought after are novel odoriferous substances which, in addition to their odorous properties, exhibit additional positive secondary properties, such as for example higher stability, higher yield, better tenacity, booster effect etc.

It was accordingly the object of the present invention to provide a new odoriferous substance which has excellent odorous properties and may be stably combined with a plurality of further odoriferous substances. Preferably, the odoriferous substance to be provided should be suitable for combining with lily of the valley odoriferous substances and advantageously suitable for imparting the impression, in combination with these lily of the valley odoriferous substances, of flowery freshness.

Said object is achieved according to the invention by the compound 3-methylbenzyl isobutyrate already mentioned above. This compound surprisingly has green appley odour properties, which are particularly well suited to achieving green fruity head notes in perfume oil mixtures, as are often desired.

BACKGROUND OF THE INVENTION

The ester according to the invention and its odour are not known from the prior art. Our own investigations into structurally similar compounds have led to the following odour descriptions.

The structurally closest compounds 2-methylbenzyl isobutyrate and 4-methylbenzyl isobutyrate were assessed overall as uninteresting from the point of view of odour and with regard to perfumery. In comparison to the compound 3-methylbenzyl isobutyrate according to the invention, surprisingly no fruity notes were detected with regard to either compound. The odour descriptions for the two compounds are as follows:

2-methylbenzyl isobutyrate: fatty, linalool, carbinol
4-methylbenzyl isobutyrate: fatty, anise, heliotrope.
4-Isopropylbenzyl isobutyrate, which is already known from the literature, only has a watery, cumin-like, herbaceous odour with anise features.
4-Methoxybenzyl isobutyrate, which is likewise already known from the literature, exhibits a pronounced odour of anise, and 2-methoxybenzyl isobutyrate smells of cinnamon and guaiac.

In S. Arctander, Perfume and Flavor Chemicals, Vols. I and II, Montclair, N.J., 1969, private publication, benzyl isobutyric acid ester is described as having a fruity-flowery fragrance and use in fruity-spicy-herbaceous odoriferous substance mixtures is indicated. A. Müller, Parfümeur, 2, 43-44, 1928 describes the fragrance of this ester as fruity, with an undertone of caraway.

SUMMARY OF THE INVENTION

The ester 3-methylbenzyl isobutyrate according to the invention thus has odour properties which were not foreseeable.

An odoriferous substance mixture according to the invention comprises organoleptically active quantities of 3-methylbenzyl isobutyrate and at least one further odoriferous substance. The ratio by weight of 3-methylbenzyl isobutyrate to the further odoriferous substances should preferably be in the range from 1:1000 to 1:5.

Advantageously, this at least one further odoriferous substance imparts a lily of the valley odour. This combination of 3-methylbenzyl isobutyrate and an odoriferous substance with lily of the valley odour is particularly preferred, since 3-methylbenzyl isobutyrate surprisingly imparts the impression of a complementary, flowery freshness even in low concentration, which is in addition to the green appley head notes of 3-methylbenzyl isobutyrate and the odour impressions imparted by the lily of the valley odoriferous substances.

Particularly advantageous is the combination of 3-methylbenzyl isobutyrate with the lily of the valley odoriferous substance 2,2-dimethyl-3-(3-methylphenyl) propanol (Majantol®). The ratio by weight of 3-methylbenzyl isobutyrate to Majantol is preferably in the range from 1:1000 to 1:5, preferably 1:100 to 1:5, more preferably 1:50 to 1:5.

The combination of 3-methylbenzyl isobutyrate with Majantol is particularly preferred for two reasons. On the one hand, even small quantities of 3-methylbenzyl isobutyrate modify the (in any case already excellent) odorous properties of Majantol, making it more flowery fresh. On the other hand, it is possible with suitable control of the process to produce 3-methylbenzyl isobutyrate and the conventional precursors of Majantol, namely 2,2-dimethyl-3(3-methylphenyl)-propionaldehyde in parallel in a common reaction batch, see in detail below. In a subsequent reaction it is then possible selectively (and without previous separation of one of the two reaction products) to hydrogenate the aldehyde to yield Majantol. The resultant final product mixture contains the odoriferous substances 3-methylbenzyl isobutyrate and Majantol.

3-Methylbenzyl isobutyrate may therefore (according to the invention) be used as odoriferous substance, in particular to impart a green fruity head note in an odoriferous substance mixture and particularly preferably to produce the impression of a complementary flowery freshness in combination with lily of the valley odoriferous substances. In addition to use in odoriferous substance mixtures, 3-methylbenzyl isobutyrate may constitute an organoleptically useful or even organoleptically crucial constituent of a plurality of products. Products according to the invention comprise a carrier or a substrate and an organoleptically active quantity of 3-methylbenzyl isobutyrate in direct contact with the carrier or the substrate.

Preferred products according to the invention are selected from among the group consisting of: alcoholic perfume, body care products and household cleaning or care products. The body care products are preferably selected from the group consisting of soaps, shower gels, shampoos, bath additives, skin creams, body lotions and deodorants, and the cleaning agents are preferably selected from the group consisting of detergents, laundry rinse conditioners, air fresheners and purifiers.

3-Methylbenzyl isobutyrate may be combined with other odoriferous substances in various, different quantity ratios to yield novel perfume compositions.

DETAILED DESCRIPTION OF THE INVENTION

Examples of odoriferous substances with which the ester according to the invention may advantageously be combined are to be found for example in S. Arctander, Perfume and Flavor Materials, Vols. I and II, Montclair, N.J., 1969, private publication or K. Bauer, D. Garbe und H. Surburg, Common Fragrance and Flavor Materials, 4$^{th}$ ed., Wiley-VCH, Weinheim 2001.

The following may be mentioned in detail:

extracts of natural raw materials such as essential oils, concretes, absolutes, resins, resinoids, balsams, tinctures such as for example:

ambergris tincture; amyris oil; angelica seed oil; angelica root oil; anise oil; valerian oil; basil oil; tree moss absolute; bay oil; artemisia oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassie absolute; castoreum absolute cedar leaf oil; cedarwood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; tarragon oil; eucalyptus citriodora oil; eucalyptus oil; fennel oil; pine-needle oil; galbanum oil; galbanum resin; geranium oil; grapefruit oil; guiacwood oil; gurjun balsam; gurjun balsam oil; helichrysum absolute; helichrysum oil; ginger oil; iris root absolute; iris root oil; jasmine absolute; calmus oil; camomile oil, blue; camomile oil, Roman; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; lime oil, distilled; lime oil, pressed; linaloe oil; Litsea cubeba oil; bay leaf oil; mace oil; marjoram oil; mandarin oil; massoia bark oil; mimosa absolute; ambrette oil; musk tincture; muscatel sage oil; nutmeg oil; myrrh absolute; myrrh oil; myrtle oil; clove leaf oil; clove bud oil; neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; sage oil, Dalmatian; sage oil, Spanish; sandalwood oil; celery seed oil; spike lavender oil; star anise oil; styrax oil; tagetes oil; fir needle oil; tea tree oil; terpentine oil; thyme oil; Tolu balsam; tonka absolute; tuberose absolute; vanilla extract; violet leaf absolute; verbena oil; vetiver oil; juniper berry oil; Cognac oil; wormwood oil; wintergreen oil; ylang ylang oil; hyssop oil; civet absolute; cinnamon leaf oil; cinnamon bark oil, and fractions thereof, or constituents isolated therefrom;

individual odoriferous substances from the group comprising hydrocarbons, such as for example: 3-carene; α-pinene; β-pinene; α-terpinene; γ-terpinene; p-cymol; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols such as for example:
hexanol; octanol; 3-octanol; 2,6-dimethylheptanol; 2-methyl-2-heptanol; 2-methyl-2-octanol;(E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and the acetals thereof such as for example:
hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5, 9-undecadienal; heptanal diethylacetal; 1,1-dimethoxy-2,2,5-trimethyl-4-hexene; citronellyloxyacetaldehyde;

aliphatic ketones and the oximes thereof such as for example: 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulfur-containing compounds such as for example: 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

aliphatic nitriles such as for example: 2-nonenoic acid nitrile; 2-tridecenoic acid nitrile; 2,12-tridecadienoic acid nitrile; 3,7-dimethyl-2,6-octadienoic acid nitrile; 3,7-dimethyl-6-octenoic acid nitrile;

aliphatic carboxylic acids and the esters thereof such as for example: (E)- and (Z)-3-hexenyl formate; ethyl acetoacetate; isoamyl acetate; hexyl acetate; 3,5, 5-trimethylhexyl acetate; 3-methyl-2-butenyl acetate; (E)-2-hexenyl acetate; (E)-and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate;

acyclic terpene alcohols such as for example: citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates, 3-methyl-2-butenoates thereof;

acyclic terpene aldehydes and ketones such as for example: geranial; neral; citronellal; 7-hydroxy-3,7-dimethyloctanal; 7-methoxy-3,7-dimethyloctanal; 2,6,10-trimethyl-9-undecenal; geranyl acetone; and the dimethyl and diethyl acetals of geranial, neral, 7-hydroxy-3,7-dimethyloctanal;

cyclic terpene alcohols such as for example: menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates, 3-methyl-2-butenoates thereof;

cyclic terpene aldehydes and ketones such as for example: menthone; isomenthone; 8-mercaptomenthan-3-one; carvone; camphor; fenchone; alpha-ionone; beta-ionone; alpha-n-methyl ionone; beta-n-methyl ionone; alpha-isomethyl ionone; beta-isomethyl ionone; alpha-irone; alpha-damascone; beta-damascone; beta-damascenone;

delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8 (5H)-one; nootkatone; dihydronootkatone; alpha-sinensal; beta-sinensal; acetylated cedarwood oil (methylcedryl ketone);

cyclic alcohols such as for example: 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols such as for example: alpha-3, 3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers such as for example: cineole; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methyl propyl)-1,3-dioxane;

cyclic and macrocyclic ketones such as for example: 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone;

4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes such as for example: 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones such as for example: 1-(3,3-dimethyl-cyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl-(2,4-dimethyl-3-cyclohexen-1-yl) ketone;

esters of cyclic alcohols such as for example: 2-tert.-butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or 6-indenyl acetate; 4,7-methano-3a, 4,5,6,7,7a-hexahydro-5- or 6-indenyl propionate; 4,7-methano-3a,4,5,6,7,7a-hexahydro-5- or 6-indenyl isobutyrate; 4,7-methanooctahydro-5- or 6-indenyl acetate;

esters of cycloaliphatic carboxylic acids such as for example: allyl-3-cyclohexyl propionate; allylcyclohexyl oxyacetate; cis- und trans-methyl dihydrojasmonate; cis- und trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

araliphatic alcohols such as for example: benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1, 1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids such as for example: benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha, alpha-dimethylphenylethyl butyrate; cinnamyl acetate; 2-phenoxyethyl isobutyrate; 4-methoxybenzyl acetate;

araliphatic ethers such as for example: 2-phenyl ethyl methyl ether; 2-phenyl ethyl isoamyl ether; 2-phenyl ethyl-1-ethoxyethyl ether; phenylacetaldehyde dimethylacetal; phenylacetaldehyde diethylacetal; hydratropaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes such as for example: benzaldehyde; phenylacetaldehyde; 3-phenylpropanal; hydratropaldehyde; 4-methylbenzaldehyde; 4-methylphenylacetaldehyde; 3-(4-ethylphenyl)2,2-dimethylpropanal; 2-methyl-3-(4-isopropylphenyl)propanal; 2-methyl-3-(4-tert.-butylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl )propanal;

aromatic and araliphatic ketones such as for example: acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanol; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6', 7',8'-tetrahydro -3',5',5',6',8',8'-hexamethyl-2-acetonaphthone;

aromatic and araliphatic carboxylic acids and the esters thereof such as for example: benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenyl glycidate; ethyl-3-methyl-3-phenyl glycidate;

nitrogenous aromatic compounds such as for example: 2,4,6-trinitro-1,3-dimethyl-5-tert.-butylbenzene; 3,5-dinitro-2, 6-dimethyl-4-tert.-butyl acetophenone; cinnamonitrile;

5-phenyl-3-methyl-2-pentenoic acid nitrile; 5-phenyl-3-methylpentanoic acid nitrile; methyl anthranilate; methyl-N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexene carbaldehyde 6-isopropyl quinoline; 6-isobutyl quinoline; 6-sec.-butyl quinoline; indole; skatole; 2-methoxy-3-isopropylpyrazine; 2-isobutyl-3-methoxypyrazine;

phenols, phenyl ethers and phenyl esters such as for example: estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

heterocyclic compounds such as for example: 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones such as for example: 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Lily of the valley odoriferous substances, with which the esters according to the invention may advantageously be combined, are for example hydroxycitronellal, methoxycitronellal, cyclamen aldehyde, 1-(4-isopropyl-cyclohexyl)ethanol (Mugetanol®), 4-tert.-butyl-α-methyl dihydrocinnamaldehyde (Lilial®), cis-hexahydrocuminyl alcohol (Mayol®), 3-[4-(1,1-dimethylethyl)phenyl] propanal (Bourgeonal®), 2,2-dimethyl-3-(3-methylphenyl)propanol (Majantol®), 3-methyl-3-(3-methylbenzyl)-butan-2-ol, 2-isobutyl-4-methyltetrahydro-2H-pyran-4-ol (Florosa®), 2-methyl-3-(3,4-methylenedioxyphenyl)propanal (Heliofolal@), 4-(4-hydroxy-4-methylpentyl)-3-cyclohexene carbaldehyde (Lyral®), 4-(octahydro-4,7-methano-5H-inden-5-ylidene-butanal (Dupical®), vernaldehyde, 4-(4-methyl-3penten-1-yl)-3-cyclohexene carbaldehyde (Vertomugal®), octahydro-5-(4-methoxybutylidene)-4,7-methano-1H-indene (Mugoflor®), 2,6-dimethyl-2-heptanol (Freesiol@), 1-ethyl-1-methyl-3-phenylpropanol (Phemec®), profarnesol, dihydrofarnesol, farnesol, hydroxycitronellal dimethyl acetal, tetrahydrolinalool, ethyl linalool, hexyl benzoate; of particular interest from the point of view of odour is, as stated, the combination of 3-methylbenzyl isobutyrate and 2,2-dimethyl-3-(3-methylphenyl)propanol (Majantol®).

In perfume compositions (odoriferous substance mixtures), the total quantity used of ester according to the invention advantageously amounts to 0.05 to 50 wt. %, preferably 0.5 to 20 wt. %, relative to the entire perfume oil composition. In combination with lily of the valley odoriferous substances, the ester according to the invention is preferably used in a concentration of 0.05 to 10 wt. %, preferably 0.5 to 5 wt. %, relative to the total lily of the valley odoriferous substances. In these concentrations, the ester according to the invention, for example in combination with Majantol®, produces a specific and characteristic flowery freshness (see also Example 3 below).

Perfume oils containing the ester according to the invention may be used for perfuming in liquid form, undiluted or diluted with a solvent. Solvents suitable for this purpose are for example ethanol, isopropanol, diethylene glycol monoethyl ether, glycerol, propylene glycol, 1,2-butylene glycol, dipropylene glycol, diethyl phthalate, triethyl citrate, isopropyl myristate etc.

Moreover, perfume oils containing the ester according to the invention may be adsorbed on a carrier, which ensures both fine distribution of the odoriferous substances in the product and controlled release during use. Such carriers may be porous inorganic materials such as light sulfate, silica gels, zeolites, gypsums, clays, clay granules, aerated concrete etc. or organic materials such as woods and cellulose-based substances.

Perfume oils containing the ester according to the invention may also be microencapsulated or spray-dried or be present as inclusion complexes or as extrusion products and be added in this form to the product to be perfumed.

Optionally, the properties of the perfume oils modified in this way are further optimised with regard to more targeted fragrance release by "coating" with suitable materials, for which purpose waxy plastics such as for example polyvinyl alcohol are preferably used.

Microencapsulation of the perfume oils may be effected for example using so-called coacervation processes with the assistance of capsule materials for example of polyurethane-type substances or soft gelatins. Spray-dried perfume oils may be produced for example by spray drying an emulsion or dispersion containing the perfume oil, wherein modified starches, proteins, dextrin and vegetable gums may be used as carriers. Inclusion complexes may be produced for example by introducing dispersions of the perfume oil and cyclodextrins or urea derivatives into a suitable solvent, for example water. Extrusion products may be produced by melting the perfume oils with a suitable waxy substance and extrusion with subsequent solidification, optionally in a suitable solvent, for example isopropanol.

The perfume oils containing the ester according to the invention may be used in concentrated form, in solutions or in the above-described modified form to produce, for example, perfume extracts, eaux de parfum, eaux de toilette, shaving lotions, eaux de cologne, pre-shave products, splash colognes and perfumed tissue wipes and to perfume acidic, alkaline and neutral cleaning agents, such as for example floor cleaners, window cleaners, dishwashing detergents, bath and sanitary cleaners, scouring cream, solid and liquid toilet cleaners, pulverulent and foam carpet cleaners, liquid detergents, pulverulent detergents, laundry pretreatment agents, such as bleaches, soaking agents and stain removers, laundry rinse conditioners, laundry soaps, laundry tablets, disinfectants, and surface disinfectants as well as air fresheners in liquid or gel form or applied to a solid carrier, aerosol sprays, waxes and polishes such as furniture polishes, floor waxes and shoe polishes as well as body care products such as for example solid and liquid soaps, shower gels, shampoos, shaving soaps, shaving foams, bath oils, cosmetic emulsions of the oil-in-water, water-in-oil and water-in-oil-in water type such as for example skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products such as for example hair sprays, hair gels, strengthening hair lotions, hair rinses, permanent and semi-permanent hair dyes, hair styling agents such as cold waving and hair straightening agents, hair tonics, hair creams and lotions, deodorants and antiperspirants such as for example underarm sprays, roll-ons, deodorant sticks, deodorant creams, decorative cosmetic products such as for example eyeshadow, nail varnish, make-up products, lipstick and mascara, as well as candles, lamp oils, incense sticks, insecticides, repellents, fuels.

3-Methylbenzyl isobutyrate may be produced using generally conventional methods for producing carboxylic acid esters, for example by esterification of isobutyric acid with 3-methylbenzyl alcohol, commercially obtainable from Sigma-Aldrich, acylation of 3-methylbenzyl alcohol with isobutyric acid chloride or isobutyric anhydride or by transesterification of methyl or ethyl isobutyrate with 3-methylbenzyl alcohol.

Particular preference is given to a process (according to the invention) for producing 3-methylbenzyl isobutyrate which comprises the following steps:

producing a reaction mixture comprising the educts (a) 3-methylbenzyl alcohol and/or 3-methylbenzyl chloride and (b) isobutyric acid (2-methylpropionic acid) and/or isobutyrate and/or isobutyraldehyde and establishing reaction conditions in the reaction mixture, in which 3-methylbenzyl isobutyrate is formed from the educt directly or via intermediate steps.

It goes without saying that, if only (b) isobutyraldehyde is present, first of all the corresponding acid or the corresponding butyrate is formed from this aldehyde, before conversion to 3-methylbenzyl isobutyrate then takes place in a subsequent step. A preferred process according to the invention is one in which the reaction mixture comprises isobutyraldehyde, which is oxidised or disproportionated under the reaction conditions to yield isobutyrate.

With regard to the preferred odoriferous substance mixtures, which also comprise Majantol in addition to 3-methylbenzyl isobutyrate, a production process according to the invention is preferred in which the reaction mixture comprises 3-methylbenzyl chloride and isobutyraldehyde (2-methylpropanal) and the reaction conditions are established in the reaction mixture such that 3-methylbenzyl isobutyrate and 2,2-dimethyl-3-(3-methylphenyl)-propionaldehyde are formed simultaneously.

The 2,2-dimethyl-3-(3-methylphenyl)-propionaldehyde (Majantal) formed may then be converted into Majantol by hydrogenation or reduction, for example as is described in WO 03/089394 or EP 0 217 159 B1. It is not necessary to isolate the compound 3-methylbenzyl isobutyrate according to the invention before hydrogenation or reduction is performed. After hydrogenation or reduction, 3-methylbenzyl isobutyrate and Majantol are then present together in the product mixture.

Further aspects of the present invention are revealed by the following Examples and the appended claims.

EXAMPLE 1

3-Methylbenzyl isobutyrate 25 g (0.2 mol) of 3-methylbenzyl alcohol (Aldrich), 18 g (0.2 mol) of isobutyric acid and 0.6 g of p-toluenesulfonic acid are heated in a 500 ml three-necked flask apparatus with a water separator until the water is completely separated. Washing is then firstly performed with diluted sodium hydrogencarbonate solution and thereafter with water. After removing the toluene by distillation, the residue is distilled using a bulb tube distillation oven. 23 g of product (60% of theoretical) is obtained.

Odour: Green, apple, fruit

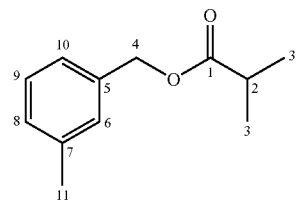

NMR spectra (200 MHz, internal standard: tetramethylsilane):
$^1$H-NMR (CDCl$_3$, ppm) δ 1.19 (d, J=7.0 Hz, 6H), 2.36 (m, J=0.7 Hz, 3H), 2.60 (septet, J=7.0 Hz, 1H), 5.07 (s, 2H), 7.09-7.31 (m, 4H).
$^{13}$C-NMR (CDCl$_3$, ppm) δ 18.9 (q), 21.3 (q), 33.9 (d), 66.0 (t), 125.0 (d), 128.3 (d), 128.6 (d), 128.7 (d), 136.1 (s), 138.0 (s), 176.6 (s).

Mass Spectrum
m/z (rel. int.): 27(4), 43(26), 71(13), 77(16), 91(8), 105 (100, bp), 122(75), 192(32, M$^+$)

EXAMPLE 2

Simultaneous Production of 3-methylbenzyl isobutyrate and 2,2-dimethyl-3-(3-methylphenyl)-propionaldehyde Reaction parameters: temperature: 45° C.; molar ratio of isobutyraldehyde: 3-methylbenzyl chloride=1.4:1

120 g of sodium hydroxide solution, 11.8 g of tetrabutylammonium iodide, 180 g of water and 310 g of toluene are introduced into a 4 l jacketed vessel and heated to 45° C. At this temperature, a mixture of 200 g of isobutyraldehyde and 290 g of 3-methylbenzyl chloride is added within 12 hours with stirring. Once addition is complete, stirring is continued for 3 hours. The batch is combined at 45° C. with 200 g water and stirred for 20 minutes. After phase separation, 566 g of alkaline aqueous phase and 748 g of organic phase are obtained.

The organic phase contains, according to gas chromatographic analysis (disregarding low-boiling components), 56.8% 2,2-dimethyl-3-(3-methylphenyl)-proionaldehyde and 3.8% 3-methylbenzyl isobutyrate. After removing the toluene in a rotary evaporator, the organic phase is distilled using a 30 cm packed column at 2.1 mbar in a temperature range of 54-62° C. 288 g of a main fraction are obtained, containing 75% 2,2-dimethyl-3-(3-methylphenyl)-proionaldehyde and 5.3% 3-methylbenzyl isobutyrate.

EXAMPLE 3

Production of a Perfume Oil with Lily of the Valley Odour Using 3-methylbenzyl isobutyrate Firstly the following components are mixed together:

| Odoriferous substance | Parts by weight |
|---|---|
| Methyl dihydrojasmonate | 50 |
| Diethyl phthalate | 61 |
| Indole | 1 |
| Geraniol | 25 |

-continued

| Odoriferous substance | Parts by weight |
|---|---|
| Phenylethyl alcohol | 50 |
| L-Citronellol | 55 |
| Hexylcinnamaldehyde | 270 |
| cis-/trans-3-Hexenyl acetate | 3 |
| Linalool | 45 |
| Linalyl acetate | 10 |
| Majantol | 80 |
| Total | 650 |

The addition of 3 parts by weight of 3-methylbenzyl isobutyrate imparts a green appley head note to the natural lily of the valley odour of the perfume oil composition. The addition of 3-methylbenzyl isobutyrate moreover gives rise to a complementary flowery freshness.

The invention claimed is:

1. An odoriferous substance mixture, comprising organoleptically active quantities of 3-methylbenzyl isobutyrate and 2,2-dimethyl-3-(3-methylphenyl) propanol, wherein the ratio by weight of 3-methylbenzyl isobutyrate to 2,2-dimethyl-3-(3-methylphenyl) propanol is in the range from 1:1000 to 1:5.

2. An odoriferous substance mixture according to claim 1, wherein the ratio by weight of 3-methylbenzyl isobutyrate to 2,2-dimethyl-3-(3-methylphenyl) propanol is in the range from 1:100 to 1:5.

3. An odoriferous substance mixture according to claim 1, comprising 3-methylbenzyl isobutyrate in a concentration of 0.05-50 wt. % relative to the total weight of the mixture.

4. An odoriferous substance mixture according to claim 1, comprising 3-methylbenzyl isobutyrate in a concentration of 0.5-20 wt. %, relative to the total weight of the mixture.

* * * * *